(12) United States Patent
Lee et al.

(10) Patent No.: US 7,581,878 B2
(45) Date of Patent: Sep. 1, 2009

(54) MEASURING SYSTEM AND SCREENING METHOD FOR THERMAL CONDUCTIVE EFFICIENCIES OF THERMAL CONDUCTIVE DEVICES

(75) Inventors: Ke-Chin Lee, Taoyuan County (TW); Chen-Chuan Lin, Taoyuan County (TW); Chi-Te Chin, Hsinchu (TW); Li-Kai Wu, Taoyuan County (TW)

(73) Assignee: Yeh-Chiang Technology Corp., Yangmei Town (TW)

( * ) Notice: Subject to any disclaimer, the term of this patent is extended or adjusted under 35 U.S.C. 154(b) by 0 days.

(21) Appl. No.: 11/317,120

(22) Filed: Dec. 22, 2005

(65) Prior Publication Data

US 2007/0047614 A1 Mar. 1, 2007

(30) Foreign Application Priority Data

Aug. 24, 2005 (TW) .............................. 94128929 A

(51) Int. Cl.
*G01N 25/18* (2006.01)
*G01N 25/20* (2006.01)
*G01K 17/06* (2006.01)

(52) U.S. Cl. .............................. 374/44; 374/29; 374/5; 374/137; 374/141

(58) Field of Classification Search ............. 374/43–45, 374/4–5, 29–30, 33, 39, 57, 135, 137, 110–112, 374/141, 147, 115; 436/149; 73/75
See application file for complete search history.

(56) References Cited

U.S. PATENT DOCUMENTS

| | | | | |
|---|---|---|---|---|
| 3,733,887 A * | 5/1973 | Stanley et al. ................. 374/44 |
| 4,504,156 A * | 3/1985 | Currie et al. ................... 374/45 |
| 4,840,495 A * | 6/1989 | Bonnefoy ...................... 374/43 |
| 5,297,868 A * | 3/1994 | Graebner ....................... 374/44 |
| 5,940,784 A * | 8/1999 | El-Husayni .................. 702/130 |
| 6,039,471 A * | 3/2000 | Wyland ......................... 374/43 |
| 6,142,662 A * | 11/2000 | Narh et al. ..................... 374/44 |
| 6,331,075 B1 * | 12/2001 | Amer et al. .................... 374/44 |
| 6,663,278 B1 * | 12/2003 | Chien et al. ................... 374/43 |
| 6,896,405 B2 * | 5/2005 | Osone et al. ................... 374/43 |
| 6,923,570 B2 * | 8/2005 | Shih et al. ...................... 374/43 |
| 6,945,691 B2 * | 9/2005 | Trapasso et al. ............... 374/15 |
| 2006/0045165 A1 * | 3/2006 | Chan et al. ..................... 374/43 |
| 2006/0256834 A1 * | 11/2006 | Chang et al. .................... 374/5 |
| 2007/0071063 A1 * | 3/2007 | Liu et al. ....................... 374/15 |
| 2008/0025364 A1 * | 1/2008 | Nakatani et al. ............... 374/12 |

* cited by examiner

*Primary Examiner*—Gail Verbitsky
(74) *Attorney, Agent, or Firm*—Bucknam and Archer

(57) ABSTRACT

The measuring system generates a temperature difference between a heating terminal and a terminal conductive device by setting the temperature of a metal heated block at the heating terminal and the temperature of a heat dissipating water jacket at a heat dissipating terminal, and judges the thermal conductive capability of the thermal conductive device by comparing the cooling speed of the metal heating bock to obtain a relative power value according to the variation of heat quantity of the metal heated block in practical temperature reduction process. The maximum thermal conductive quantity (Qmax value) of the thermal conductive device can be rapidly obtained by parameter conversion with respect to the maximum power value. In the case of confirming the cooling curve (cooling speed) of a standard sample, the object of screening the thermal conductive efficiencies of the thermal conductive devices can be achieved by using the cooling curve.

13 Claims, 3 Drawing Sheets

MEASURING SYSTEM AND SCREENING METHOD FOR THERMAL CONDUCTIVE EFFICIENCIES OF THERMAL CONDUCTIVE DEVICES

BACKGROUND OF THE INVENTION

1. Field of the Invention

The present invention relates to a measuring system and a screening method for the thermal conductive efficiencies of thermal conductive devices. In particular, the present invention is to rapidly measure the thermal conductive efficiencies of thermal conductive devices (for example, heat pipes, heat spreaders, heat sinks, etc.) so as to attain the object of screening the thermal conductive efficiencies of the thermal conductive devices, and thus can greatly reduce manpower and time cost and meet the requirements of stable reproducibility, resolution and reliability.

2. Description of the Related Art

With the trends of micro-miniaturization and multi-function of electronic products, it will bring devices and systems significant influences. Since more transistors need to be contained in a limited space and more heat thus increased to vary the work functions of the electronic devices, this will cause an extremely challenge to engineers in this area. A current traditional system heat dissipating solution mode leads heat generated by a high heat-generating device, such as CPU or VGA, into a heat sink or a metal block having a high thermal conductive property through a packaging surface layer and conducts the heat to a heat exhausting device (for example, a fan, a heat sink, etc.) through a thermal conductive device, (for example, a heat pipe, a heat spreader, etc.), so that the high-heat-generating device can operate at a constant operation temperature. It is a design concept for a basic heat dissipating module.

When a chip trends to micro-miniaturization and function integration, if heat generated per unit area can be rapidly spreaded to the whole substrate through a high thermal conductive heat pipe so as to uniformly spread and conduct the heat to heat sinks which contact with the chip and to minimize the non-stability of the device caused by local hot points, the reliability and lifetime of the device can be efficiently enhanced.

Since inner operating fluid of the heat pipe absorbs heat by the phase change between liquid and gas phases and transmits heat by gas molecules, the heat pipe can obtain a much higher thermal conductivity and has a quite good thermal conductive effect. Therefore, in the module, heat generated by a high heat-generating device, such as CPU/GPU and so on, is rapidly transmitted in the phase change inside the heat pipe, a better heat exchange way is provided by more protruding heat sinks, the heat is exhausted out to the air by a fan. The heat generated by the CPU/GPU can be took away at one time and the operating temperature is greatly reduced, it means that its heat dissipating efficiency is obviously. Therefore, how to rapidly and effectively ensure the efficiency of the heat pipe by a measuring method is a main issue which needs to be studied.

A measuring method for a traditional thermal conductive device (for example, a heat pipe) generally applies heat generated by inputting a constant power to the heating terminal of the heat pipe. When the heating terminal reaches a set temperature T1 (for example, 70° C.), a cooling device (typically, a fan or a water jacket) at a heat dissipating terminal is activated. Whether the thermal conductive capability of the heat pipe reaches the requirement of the input constant power value is judged based on if the temperature of the heating terminal can be cooled down and the temperature difference $\Delta T$ between the heating terminal (T1) and the heat dissipating terminal (T2).

Such measuring method only obtains a thermal conductive efficiency of the heat pipe at a specific heating power each time. Each measurement takes about 3 to 5 minutes. If it is required to measure the maximum thermal conductive capability (Qmax), the input power of the heating terminal must be gradually increased until the temperature of the heating terminal cannot be cooled down. At this time, the highest power value measured in the previous measurement is defined as the maximum thermal conductive capability (Qmax) of the heat pipe. The measurements from the low power to the high power typically require 5 or 6 times to obtain the Qmax value. That is, it takes 15 to 30 minutes or more in average to measure the Qmax of one heat pipe. So, it is quite time consuming.

The above-stated traditional measuring method still has a vague point on the cooling method for the cooling terminal. In general, a fan or a water jacket is frequently used to cool the cooling terminal. As for how to decide the air flow of the fan or the water flow and temperature of the water jacket, it does not be clearly defined in measurements. It merely states that its flow rate which can cool the heating terminal. Therefore, it is frequently found in practice that when the heating terminal reaches the set temperature T1, immediate after the heat dissipating module for the cooling terminal is activated, if the flow rate is too large at the first time, it may cause a dry out effect to the heat pipe; however, if the flow rate is slowly increased, the heat pipe does not have the dry out effect and can cool down the temperature of the heating terminal. From the above, it is obvious that the control of the flow rate will affect the result of the measurement. If it is required to obtain a precise. Qmax value, the control of the flow rate becomes quite important since the thermal conductive capability of one heat pipe is constant at the same operation condition. However, this part does not be strictly defined on current measurement standard. In other words, not only the traditional measuring method consumes more manpower and time cost, but also the reproducibility, resolution and reliability of the measurements are unstable, so its application value is low.

SUMMARY OF THE INVENTION

In viewing of that the traditional measuring method of thermal conductive devices cannot satisfy the requirements of current thermal conductive device's quantification and reliability, an object of the present invention is to provide a measuring system for the thermal conductive efficiencies of thermal conductive devices, which is applied to swiftly measure the thermal conductive efficiencies of thermal conductive devices (for example, heat pipes, heat spreader, heat sinks, etc.) so as to attain the objects of fast quantification and screening, and manpower and time cost are greatly reduced.

In order to achieve the objects and other objects, a measuring system for the thermal conductive efficiencies of thermal conductive devices according to the present invention comprises: a heating module, located at the heating terminal of a thermal conductive device to be measured, the heating module comprising a metal heated block which is heated by a heating rod; a heat dissipating module, located at the heat dissipating terminal of the thermal conductive device to be measured, the heat dissipating terminal being cooled by for example a water jacket and so on; a temperature extraction interface module, for measuring the metal heated block and extracting corresponding values of temperature and time; and a calculation module, for calculating a simulation heat dissipated quantity (Q) of the metal heated block at maximum temperature drop by a calculation software, based on the measured value of the temperature extraction interface module, and further comparing it with a database to correspond a maximum power value of the thermal conductive device. Thus, the temperature of the metal heated block at the heating terminal and the temperature of the water jacket at the heat dissipating terminal are set to generate the temperature difference between the heating terminal and the heat dissipating terminal, and the cooling speed of the heated block is determined accordingly to judge the thermal conductive capability of the heat pipe. At the same time, a relative power value can be obtained according to the variation of heat quantity of the heated block in practical temperature reduction process, and the maximum thermal conductive quantity (Qmax value) of the heat pipe can be rapidly obtained by parameter conversion with respect to the maximum power value.

Another object of the present invention is to provide a screening method for the thermal conductive efficiencies of thermal conductive devices. In the case of confirming the cooling curve (cooling speed) of a standard sample in conjunction with the above-stated measuring system, the object of screening the thermal conductive efficiencies of the thermal conductive devices is achieved by using the cooling curve. With the measuring system and screening method for the thermal conductive efficiencies of the thermal conductive devices, the measuring time can be greatly reduced to 1 to 3 minute(s). As compared with the prior measuring method used in the current industry, manpower and time cost can be greatly reduced, and the requirements of stable reproducibility, resolution and reliability are achieved.

DESCRIPTION OF THE PREFERRED EMBODIMENTS

A measuring system and a screen method for the thermal conductive efficiencies of thermal conductive devices according to the present invention is to rapidly measure the thermal conductive efficiencies (for example, temperature difference ΔT, contact thermal resistance R and maximum thermal conductive quantity Qmax, etc.) of thermal conductive devices (for example, heat pipes, heat spreader, heat sinks, etc.) so as to attain the objects of fast quantification and screening. In the following embodiment, a heat pipe to be measured 10' is used to further explain the technical features of the present invention. The embodiment is merely a preferred example, and is not used to limit the scope of the present invention. The present invention can become more fully understood from the following detailed descriptions with reference to the accompanying drawings.

Figure 1:
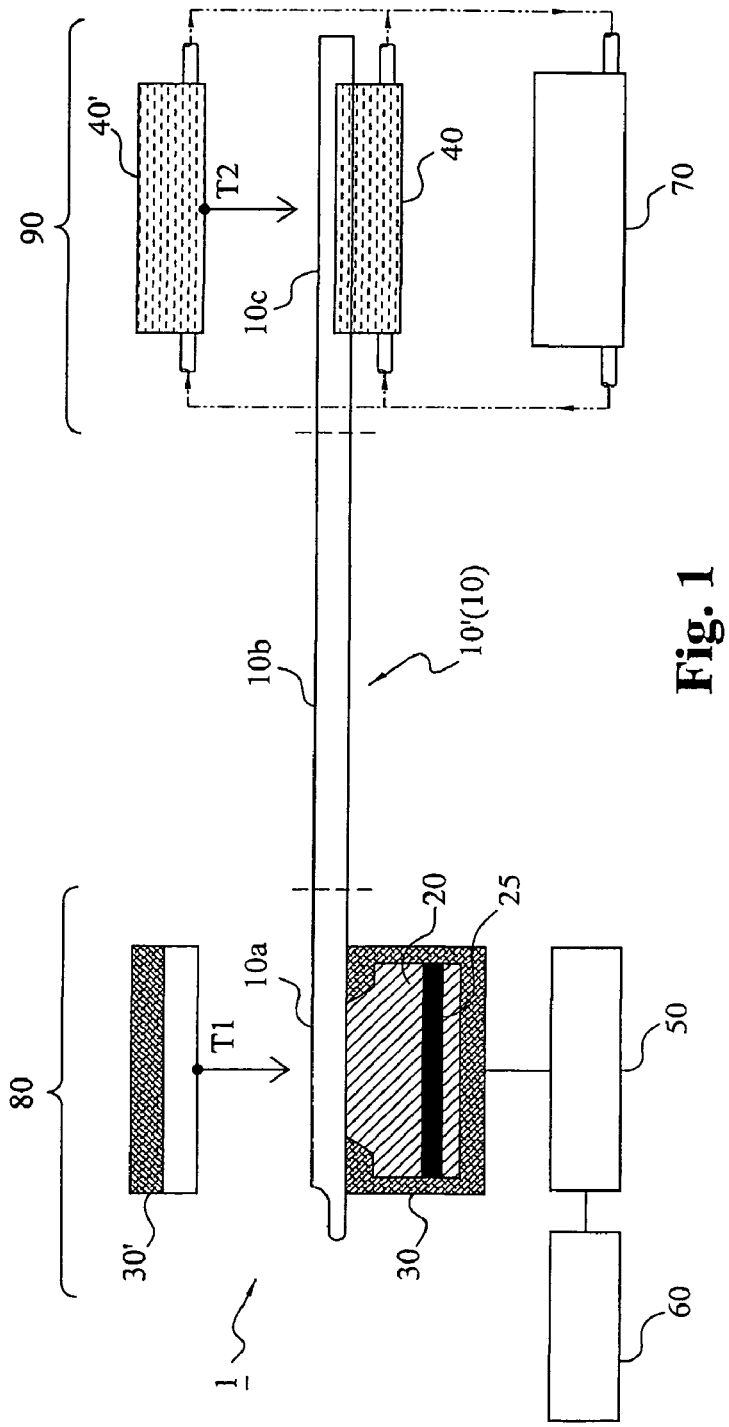
FIG. 1 is a schematic view of a measuring system for the thermal conductive efficiencies of thermal conductive devices according to an embodiment of the present invention.

First, referring to FIG. 1, a schematic view of a measuring system 1 for the thermal conductive efficiencies of thermal conductive devices according to the present invention is shown. The measuring system mainly comprises:

a heat pipe 10' to be measured, having a heating terminal (region) 10a, a heat insulating terminal 10b and a heat dissipating terminal 10c according to its thermal conductive direction;

a heating module 80, comprising a metal heated block 20 located at the heating terminal 10a of the heat pipe 10', the metal heated block 20 having a heating rod 25 inside, used to heat the metal heated block 20;

a heat insulating box 30, made of an insulating material such as bakelite and enclosing the metal heated block 20 for blocking heat from being spreaded into air;

a heat insulating pressure device 30', made of an insulating material such as bakelite and applying a pressure relatively to and covering the outer surface of the heating terminal 10a for blocking heat from being spreaded into the air;

a heat dissipating module 90, comprising a cooling device 40 (for example, a water jacket and so on) located at the heat dissipating terminal 10c of the thermal conductive device 10, and a cooling pressure device 40', applying a pressure relatively to and being attached to the surface of the heat dissipating terminal 10c, for cooling the heat dissipating terminal 10c based on its temperature difference sensible heat, wherein the cooling water of the water jacket pair 40 and 40' constructs a circulation by using a constant temperature water tank 70; furthermore, the persons skilled in the art realize that the heat dissipating module 90 can also be joined to the heat insulating terminal 10b of the heat pipe 10' (as FIG. 1 shown) depending on the designs and verifications of different heat pipes;

a temperature extraction interface module 50, for extracting corresponding temperature values of the metal heated block 20 varying with time during the cooling, the function of extracting temperature and corresponding time being able to be achieved in cooperation with a temperature extraction card or a temperature recorder in design; and a calculation module 60, for calculating a simulation heat dissipated quantity (Q) of the metal heated block at maximum temperature drop by a calculation software, based on a corresponding curve of temperature and time extracted by the temperature extraction interface module 50.

Figure 1A:
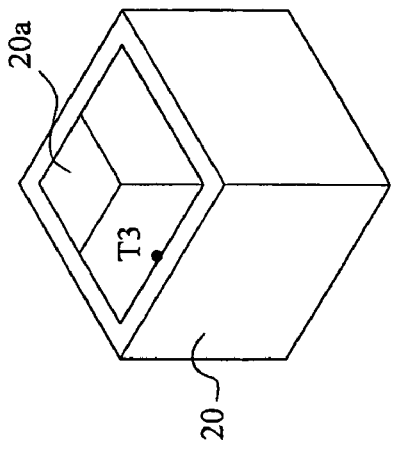
FIG. 1a is a schematic perspective view of a metal heated block according to the present invention.
Figure 3:
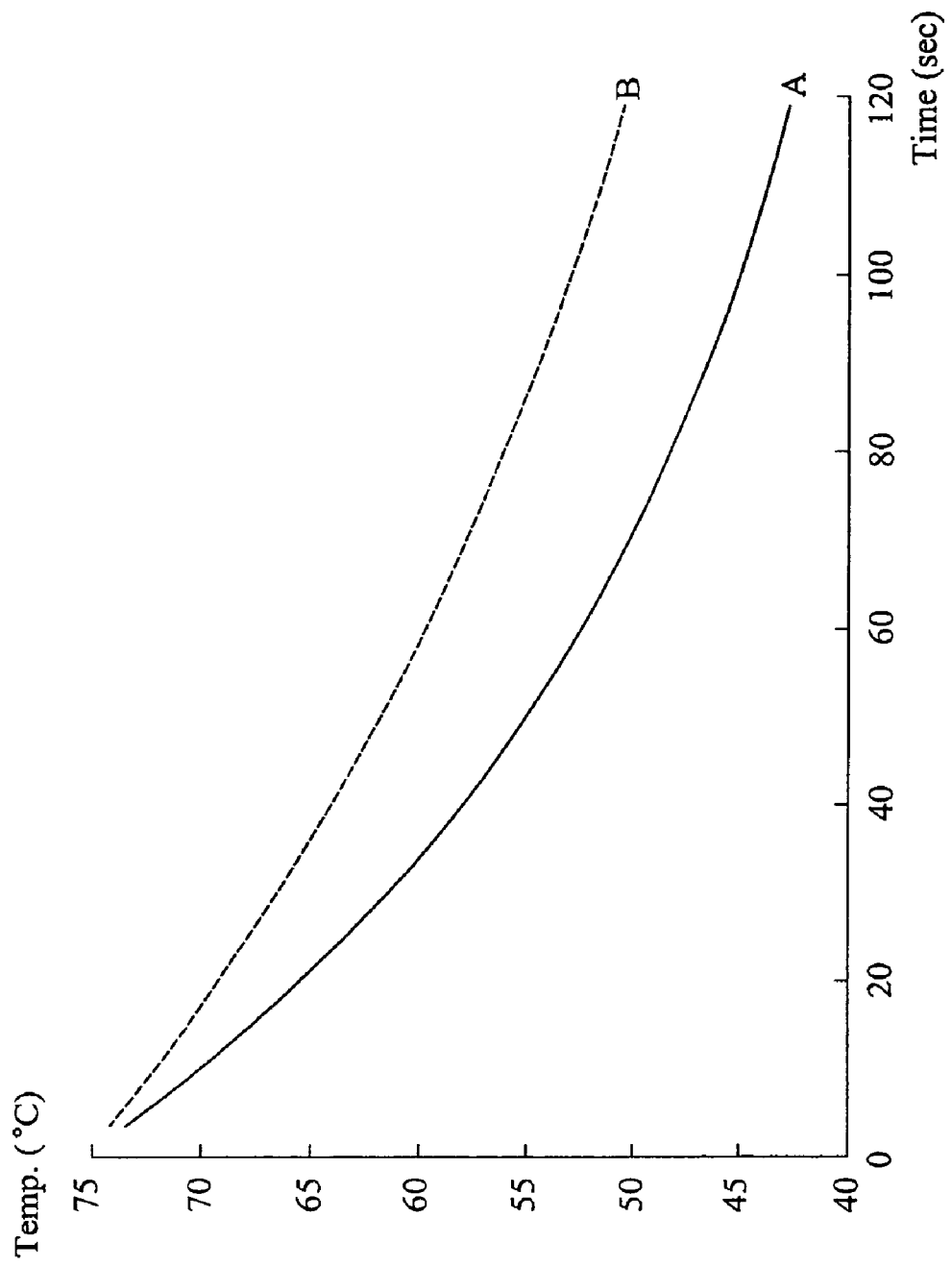
FIG. 3 is a diagram for judging the thermal conductive functions of thermal conductive devices according to the present invention.

According to the present invention, the metal heated block 20 can be metal, such as copper, aluminum, zinc etc., or composite material having a high thermal conductive capability (thermal conductive value) and low heat capacity ratio, to ensure the uniform temperature of the metal heated block during the heat dissipating and cooling process. Preferably, the metal heated block 20 is of a trapezoid structure (as FIG. 1a shown), which can effectively enhance the thermal conductive efficiency so as to obtain a uniform temperature effect and to prevent heat loss. Except that the top joint face 20a of the trapezoid heated block structure is jointed to the heating terminal 10a of the heat pipe 10', the outer surface thereof is enclosed by the heat insulating box 30 made of an insulating material to form a much better heat insulating environment together with the heat insulating pressure device 30'. When the metal heated block 20 of the heating module 80 is heated to a specific temperature (for example, 80° C.) and maintained at a static state under a constant input power, the temperature difference (ΔT) between the surface temperature T1 of the heating terminal 10a and the surface temperature T2 of the heating dissipating terminal 10c at the heat pipe 10' is recorded to be a functional judgment at the first phase (for example, ΔT<3° C.). Then, the heating is stopped, and the metal heated block 20 is cooled by using the heat dissipating module 90. At this time, the heat pipe 10' is a good thermal conductive device. Simultaneously, the temperature extraction interface module 50 extracts corresponding values of temperature T3 and time from the metal heated block 20 of the heating module 80 during the cooling. Then, the value extracted by the temperature extraction interface module 50 is input to the calculation module 60 to obtain a corresponding curve between temperature and time through a software operation (as FIG. 3 shown).

According to the present invention, the calculation module 60 can obtain a heat dissipating quantity (Q) through an operation by using a calculation software self-developed by the present inventors, from the extracted corresponding curve of temperature and time in cooperation with a thermophysical equation $Q=W \cdot Cp \cdot (dT/dt)$, where W is the weight of the metal heated block 20, Cp is a heat capacity, and dT/dt is a temperature-time differential equation. Then, the contact thermal resistance of the metal heated block 20 and the heat pipe 10 is obtained by substituting the heat dissipating quantity (Q), the surface temperature T1 of the heat pipe and the temperature T3 of the heated block into a thermal resistance equation $R_{Contact}=(T1-T3)/Q$, which can serve as a functional judgment at the second phase (for example, $R_{Contact}<X$). At this point, a simulation heat dissipating quantity (Q) is obtained by judging a maximum temperature drop (dT/dt) in a specific time interval using the calculation software, so as to serve as a function judgment at the third phase GO/NO GO (for example, Q>30 watts). Furthermore, the simulation heat dissipating quantity (Q) is compared with a database to find out an approximate maximum thermal conductive power value (Qmax) of the heat pipe 10'.

Figure 2:
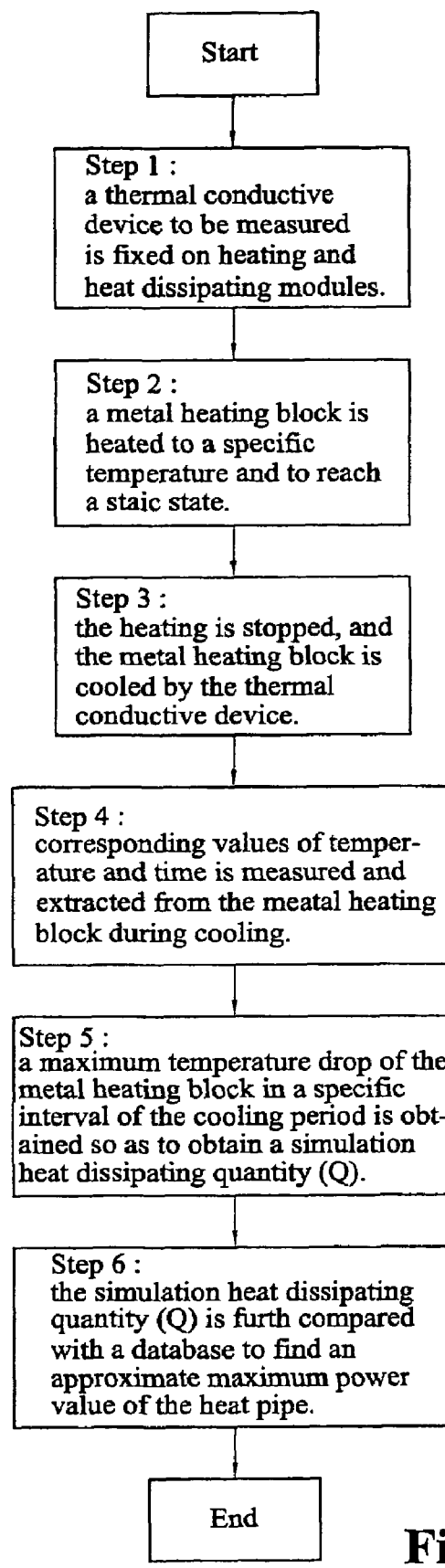
FIG. 2 is a flow chart of a screening method for the thermal conductive efficiencies of thermal conductive devices according to the present invention.

According to the present invention, a screening method for the thermal conductive efficiencies of thermal conductive devices must be performed in cooperation with the measuring system. In order to clearly and systematically explain the rapidly screening method of the present invention, please refers to FIG. 2.

First, the heating terminal 10a of the heat pipe 10' to be measured is fixed on the heating module 80, and the heat dissipating terminal 10c is fixed on the heat dissipating module 90 (Step 1).

Then, the metal heated block 20 of the heating module 80 is heated to a specific temperature and to reach a static state (about 1~1.5 minute(s)) (Step 2).

The heating is stopped, and the metal heated block 20 is cooled by the heat pipe 10' (Step 3).

During the cooling step, the temperature extraction interface module 50 measures and extracts corresponding values of temperature and time from the heated block 20 (about 0.5~1 minute) (Step 4).

A maximum temperature drop of the meal heated block 20 in a specific interval of the cooling period is obtained from the values extracted by temperature extraction interface module 50, through the calculation module 60's operation so as to obtain a simulation heat dissipating quantity (Q) (Step 5).

The simulation heat dissipating quantity (Q) is compared with the database to find out an approximate maximum thermal conductive capability (Qmax) of the heat pipe 10' (Step 6).

The measuring method of the present invention is based on the property of the heat pipe having the same type (the same shape and design). When an input power is higher than a certain constant value, the thermal conductive capability (Q) and the maximum thermal conductive capability (Qmax) of the heat pipe has a proportional relationship. For example, two heat pipes A and B (the Qmax value of the heat pipe A is 80 W, and the Qmax value of the heat pipe B is 70 W) are attached to the heated block having a constant heat capacity, The heat pipe A has a better thermal conductive capability than the heat pipe B. That is, as compared with the heat pipe B, the heat pipe A makes the heat block be more rapidly cooled (as FIG. 3 shown).

In order to practically compare the prior measuring method for heat pipes' efficiencies with the rapidly measuring method of the present invention, the following experiment is conducted by using the embodiment of the present invention.

Ten same type heat pipes are measured by the prior measuring method and the measuring method of the embodiment of the present invention, respectively, to verify time taken by the two methods and other different values. The measuring result is listed as follows (shown in Table 1):

TABLE 1

| U-type pipe 6 × 220 | ΔT (T1 − T2) | Qmax, mapping (the present invention) | Time (the present invention) (min.) | Qmax (the prior art) | Time (the prior art) (min.) | Qmax Power Error | Error |
| --- | --- | --- | --- | --- | --- | --- | --- |
| 1 | 0.5 | 46.42 | 1.5 | 46 | >20 | 0.42 | 0.9% |
| 2 | 0.8 | 45.01 | 1.5 | 44 | >20 | 1.01 | 2.3% |
| 3 | 3.2 | 37.50 | 1.5 | 38 | >20 | −0.50 | −1.3% |
| 4 | 0.6 | 42.21 | 1.5 | 44 | >20 | −1.79 | −4.1% |
| 5 | 1.2 | 44.61 | 1.5 | 43 | >20 | 1.61 | 3.7% |
| 6 | 0.1 | 43.61 | 1.5 | 44 | >20 | −0.39 | −0.9% |
| 7 | 1 | 42.42 | 1.5 | 42 | >20 | 0.42 | 1.0% |
| 8 | 0.1 | 49.24 | 1.5 | 48 | >20 | 1.24 | 2.6% |
| 9 | 1.6 | 44.26 | 1.5 | 46 | >20 | −1.74 | −3.8% |
| 10 | 1.3 | 46.69 | 1.5 | 46 | >20 | 0.69 | 1.5% |

It is obvious from the measuring result of Table 1 that in the measuring method for heat pipes' efficiencies according to the embodiment of the present invention and the prior measuring method, the errors of the maximum thermal conductive quantities Qmax can all be maintained within 5%, but the measuring time of the present invention can be shorten to within 3 minutes. Moreover, as shown in ΔT of the third heat pipe, serving as a screening method, the heat pipe having insufficient thermal conductive quantity can be first and effectively screened out. Therefore, a measuring system and a screening method for the thermal conductive efficiencies of thermal conductive devices according to the present invention is not only suitable for screening the thermal conductive quantities of heat pipes, but also greatly reduce manpower and time cost, so as to achieve the requirements of stable reproducibility, resolution and reliability.

The above preferred embodiment of the present invention is illustrative only, it is not used to limit the scope of the invention. The equivalent changes and modifications not departing from the claims below should still pertain to the scope of the invention.

LIST OF MAJOR ELEMENTS AND ITS CORRESPONDING REFERENCE NUMERALS 1 measuring system
10 thermal conductive device
10' heat pipe to be measured
10a heating terminal
10b heat insulating terminal
10c heat dissipating terminal
20 metal heated block
20a joint face
25 heating rod
30 heat insulating box
30' heat insulating pressure device
40 cooling device/water jacket
40' cooling pressure device/water jacket
50 temperature extraction interface module
60 calculation module
70 constant temperature water tank
80 heating module
90 heat dissipating module

What is claimed is:

1. A measuring system (1) for determining the approximate maximum thermal conductive capability (Qmax) of a thermal conductive device (10), the thermal conductive device (10) to be measured comprising a heating terminal (10a) and a heat dissipating terminal (10c), the measuring system (1) comprising:
a heating module (80), comprising a metal heated block (20) located at the heating terminal (10a) of the thermal conductive device (10), a heating rod (25) used for heating the metal heated block (20) to a predetermined temperature, and a heat insulating pressure device (30') used for applying a pressure relatively to and covering the surface of the heating terminal (10a);
a heat dissipating module (90), located at the heat dissipating terminal (10c) of the thermal conductive device (10), wherein a cooling device (40) cools the heat dissipating terminal (10c) and a cooling pressure device (40') applies a pressure relatively to and is joined to the surface of the heat dissipating terminal (10c);
a temperature extraction interface module (50), for extracting corresponding temperature values of the metal heated block (20) varying with time during cooling; and
a calculation module (60) which obtains a maximum temperature drop of the metal heated block (20) in a specific interval of the cooling period from the values extracted by the temperature extraction interface module (50) from which a simulation heat dissipated quantity (Q) is obtained and compared with a database to obtain the approximate maximum thermal conductive capability (Qmax) of the thermal conductive device (10).

2. The measuring system (1) as claimed in claim 1, wherein the metal heated block (20) is selected from one of copper, aluminum, zinc.

3. The measuring system (1) as claimed in claim 2, wherein the metal heated block (20) is of a trapezoid structure, except that the top of the trapezoid heated block structure is a joint face (20a), its outer surface is enclosed by a heat insulating box (30) made of an insulating material.

4. The measuring system (1) as claimed in claim 3, wherein the heat insulating material is bakelite.

5. The measuring system (1) as claimed in claim 1, wherein the heat insulating pressure device (30') is made of an heat insulating material, bakelite.

6. The measuring system (1) as claimed in claim 1, wherein the cooling device (40) and the cooling pressure device (40') is a water jacket, and the cooling water of the cooling device (40) and the cooling pressure device (40') constructs a circulation through a constant temperature water tank (70).

7. The measuring system (1) as claimed in claim 1, wherein the calculation software applies a thermophysical equation $Q = W \cdot C_p \cdot (dT/dt)$, where W is the weight of the metal heated block, Cp is a heat capacity of the metal heated block, and dT/dt is a temperature-time differential equation, a heat dissipating quantity (Q) being obtained through an operation by using the thermophysical equation.

8. The measuring system (1) as claimed in claim 7, wherein the calculation software applies a thermal resistance equation $R_{contact} = (T1-3)/Q$, where Q is the heat dissipating quantity, T1 is the surface temperature of the thermal conductive device, and T3 is the temperature of the metal heated block, a contact thermal resistance ($R_{contact}$) between the metal heated block and the thermal conductive device being obtained through an operation by using the thermal resistance equation.

9. The measuring system (1) as claimed in claim 1, wherein the thermal conductive device (10) is a heat pipe (10').

10. A screening method for determining the approximate maximum thermal conductive capability (Qmax) of a thermal conductive device, applied for rapidly measuring the capability of thermal conductive device (10), the thermal conductive device (10) comprising a heating terminal (10a) and a heat dissipating terminal (10c), the method comprising the steps of:
step 1: fixing the heating terminal (10a) of the thermal conductive device (10) to be measured on a heating module (80), and fixing the other heat dissipating terminal (10c) on a heat dissipating module (90);
step 2: heating a metal heated block (20) on the heating module (80) to a specific temperature and to reach a static state;
step 3: stopping the heating, and cooling the metal heated block (20) by the thermal conduction of the thermal conductive device (10);
step 4: measuring and extracting corresponding values of temperature and time from the heated block (20) during cooling;
step 5: finding a maximum temperature drop of the metal heated block (20) in a specific interval of the cooling period, so as to obtain a simulation heat dissipating quantity (Q); and
step 6: comparing the simulation heat dissipating quantity (Q) with a database to find out an approximate maximum thermal conductive capability (Qmax) of the thermal conductive device 10.

11. The screening method as claimed in claim 10, wherein the thermal conductive device (10) is a heat pipe.

12. The screening method as claimed in claim 11, wherein a heat dissipating quantity (Q) is obtained through an operation by using a thermophysical equation $Q = W \cdot C_p \cdot (dT/dt)$, wherein dT/dt is the corresponding values of temperature and time which are measured from the metal heated block during cooling, W is the weight of the metal heated block, and Cp is a heat capacity of the metal heated block.

13. The screening method as claimed in claim 12, wherein a contact thermal resistance ($R_{contact}$) between the metal heated block and the thermal conductive device is obtained through an operation by using a thermal resistance equation $R_{contact}(T1-T3)/Q$, where Q is the heat dissipating quantity, T1 is the surface temperature of the thermal conductive device, and T3 is the temperature of the metal heated block.

* * * * *